(12) United States Patent
Yun et al.

(10) Patent No.: US 9,347,939 B2
(45) Date of Patent: May 24, 2016

(54) METHOD FOR MAKING POLYMER SINGLE NANOWIRES AND SENSORS UTILIZING THE SAME

(71) Applicants: Minhee Yun, Pittsburgh, PA (US); David Schwartzman, Pittsburgh, PA (US); Jiyong Huang, Pittsburgh, PA (US)

(72) Inventors: Minhee Yun, Pittsburgh, PA (US); David Schwartzman, Pittsburgh, PA (US); Jiyong Huang, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/901,532

(22) Filed: May 23, 2013

(65) Prior Publication Data

US 2014/0154785 A1    Jun. 5, 2014

Related U.S. Application Data

(60) Provisional application No. 61/650,575, filed on May 23, 2012.

(51) Int. Cl.
*B82Y 40/00* (2011.01)
*B82Y 15/00* (2011.01)
*G01N 33/543* (2006.01)
*G01N 27/414* (2006.01)

(52) U.S. Cl.
CPC ...... *G01N 33/54373* (2013.01); *G01N 27/4145* (2013.01); *G01N 27/4146* (2013.01); *G01N 33/54366* (2013.01); *B82Y 15/00* (2013.01); *Y10S 977/762* (2013.01)

(58) Field of Classification Search
CPC ............ G01N 33/54373; G01N 33/54366; G01N 27/4145; G01N 27/4146; B82Y 15/00; Y10S 977/762
USPC .............. 977/840, 890–892, 895–897
See application file for complete search history.

(56) References Cited

PUBLICATIONS

Lee, Innam, et al. "Highly sensitive single polyaniline nanowire biosensor for the detection of immunoglobulin G and myoglobin." Biosensors and Bioelectronics26.7 (Jan. 6, 2011): 3297-3302.*
Luo, Xinyan. "Ultrasensitive protein detection using an aptamer-functionalized single polyaniline nanowire." Chemical Communications 47.22 (May 6, 2011): 6368-6370.*
Yunus, Sami, Anne Attout, and Patrick Bertrand. "Controlled aniline polymerization strategies for polyaniline micro- and nano self-assembling into practical electronic devices." Langmuir 25.3 (Jan. 6, 2009): 1851-1854.*

* cited by examiner

*Primary Examiner* — Lyle Alexander
*Assistant Examiner* — Robert Eom
(74) *Attorney, Agent, or Firm* — Paul D. Bangor, Jr.; Clark Hill, PLC (57) ABSTRACT

A method of fabricating polymer single nanowires, comprising the steps of: spin coating a polymethylmethacrylate resist onto a silicon wafer patterned with at least one gold electrode pair; creating a nanochannel using e-beam lithography between each pair of the at least one gold electrode pairs; placing the silicon wafer into an aniline monomer polymerization solution; reacting the polymerization solution to give a coated wafer and a polyaniline film; and cleaning the coated wafer of polymethylmethacrylate resist and polyaniline film to give at least one gold electrode pair with a connecting polymer single nanowire.

3 Claims, 6 Drawing Sheets

METHOD FOR MAKING POLYMER SINGLE NANOWIRES AND SENSORS UTILIZING THE SAME

RELATED APPLICATION

This application claims priority benefit under 35 U.S.C. §119(e) of U.S. Provisional Application No. 61/650,575, filed May 23, 2012, the contents of which are herein incorporated by reference.

GOVERNMENTAL RIGHTS

This invention was made with government support under Grant No. EB008825 awarded by the National Institutes of Health (NIH). The government has certain rights in the invention.

TECHNICAL FIELD

The present disclosure generally relates to the manufacture of electrically conducting single nanowires having a consistently reproducible diameter, the nanowires capable of modification as a component of biological sensors able to quantitatively and qualitatively measure levels of biomarkers such as B-type natriuretic peptide (BNP).

BACKGROUND

Nanowires are man-made structures on the scale of nanometers that are used in miniature electronic circuits such as amplifiers and transistors. It is known in the art to functionalize these nanowires so that they are able to detect the presence of a certain molecule in a volume of air or liquid. Typically, these devices, which are also known by the term "lab-on-a-chip," have nanowires that have been treated so that the resistance to electrical current through them changes when the nanowire is in the presence of the molecule of interest. When the resistance in the nanowire changes, the voltage change across the nanowire can easily be measured and thus the substance of interest can be detected. Mass production of single functional nanowires of uniform diameter has proven to be extremely difficult, however, because the prior art methods of production result in bundled nanowires of non-uniform width and quality. Uniformity of diameter is important so that devices all start with the same initial conductance.

One important use for these functionalized or surface modified nanowires with antibodies is to place them across channels through which fluids to be analyzed can pass. These so-called microfluidic devices have been designed to detect the presence of a wide range of chemicals, biological triggers and other biomarkers.

Cardiovascular disease claims about thirty-two lives per second, world wide, and in the United States, claims two lives per minute according to published statistics. B-type natriuretic peptide (BNP) is a biomarker for Myocardial Infarction and is used in hospitals and emergency rooms (ER) to monitor Cardiovascular disease (CVD) patients. BNP is a biomarker for myocardial infarction because it is well-known that when a patient's heart failure symptoms begin or worsen, the ventricles in the heart secrete BNP, causing an elevated level of the marker in the blood. Generally speaking, the greater the BNP level in the blood, the more severe the condition.

This correlation between heart failure and BNP is well known and it is routine to test for BNP in the blood of a patient presenting in an emergency room complaining of shortness of breath or some other symptom of heart failure, especially when there is a suggestive history of this type of problem. The drawback to this emergency room test, however, is that instead of predicting a heart problem, it is relegated to confirming the source of symptoms the patient is complaining of in the emergency room—well after the onset of the negative heart event.

What is needed is a way to monitor this biomarker on a regular basis for those at an elevated risk of heart failure so that a negative event can be caught much earlier, preferably outside the health care system setting, resulting in better care at a lower overall cost due to reduced incidence of hospitalization. While BNP levels are generally measured in hospitals and ERs, there is no system offering high sensitivity, extreme selectivity and low cost for the detection of BNP that can be used for a CVD patient to test BNP levels at home.

SUMMARY

One aspect of a preferred embodiment of the present disclosure comprises a method of fabricating polymer single nanowires, comprising the steps of: spin coating a polymethylmethacrylate resist onto a silicon wafer patterned with at least one gold electrode pair; creating a nanochannel using e-beam lithography between each pair of the at least one gold electrode pairs; placing the silicon wafer into an aniline monomer polymerization solution; reacting the polymerization solution to give a coated wafer and a polyaniline film; and cleaning the coated wafer of polymethylmethacrylate resist and polyaniline film to give at least one gold electrode pair with a connecting polymer single nanowire. Preferably, there is a plurality of gold electrode pairs on the silicon wafer; each of the polymer single nanowires has a uniform diameter; and/or each polymer single nanowire has a diameter of about 100 nanometers and a length of about 8 micrometers.

In another aspect of a preferred embodiment of the present disclosure, a polymer single nanowire has a plurality of polymer nanofibers whereby the surface to volume ratio is elevated. Furthermore, such preferred polymer single nanowire may comprise polyaniline.

Yet an additional aspect of a preferred embodiment of the present disclosure comprises a method of functionalizing polymer single nanowires to enable detection of a biomarker for a certain disease comprising the steps of: incubating an aqueous mixture of 1-ethyl-3-(3-dimethylaminopropyl) carbodiimide), N-hydroxysuccinimide, and a biomarker on a polymer single nanowire that connects a pair of gold electrodes on a silicon wafer; rinsing the polymer single nanowire; and soaking the polymer single nanowire in an aqueous solution of bovine serum albumin Preferably, the biomarker is selected from the group consisting of B-type natriuretic peptide, myoglobin (Myo), cardiac troponin (cTpI), and creatine kinase (CK-MB).

A further of a preferred embodiment of the present disclosure comprises a method of manufacturing microfluidic sensors using functionalized polymer single nanowires, comprising the steps of: covalently bonding a biomarker to each of a plurality of polymer single nanowires, wherein each polymer single nanowire connects two gold electrodes on a silicon wafer to give a plurality of prefunctionalized biosensors; and integrating polydimethylsiloxane with each of the plurality of prefunctionalized biosensors using oxygen plasma treatment to give a plurality of microfluidic sensors. Preferably, such method further comprises the step of shielding each of the plurality of functionalized polymer single nanowires during oxygen plasma treatment. Such shielding preferably comprises a shadow mask wherein the shadow mask may preferably comprise an aluminum substrate. Additionally, the silicon wafer preferably has at least sixteen pairs of gold electrodes thereon.

In another aspect of a preferred embodiment of the present disclosure comprises a biosensor comprising a microfluidic biosensor having an ion-sensitive field-effect transistor. Preferably, the transistor comprises a biomarker functionalized polymer single nanowire and/or the functionalized polymer single nanowire comprises polyaniline.

A further of a preferred embodiment of the present disclosure comprises a method of biasing a microfluidic biosensor to maximize sensitivity to a biomarker, the method comprising the steps of: covalently bonding the biomarker to a polymer single nanowire connecting two electrodes on a silicon wafer to give a prefunctionalized biosensor; integrating polydimethylsiloxane with the prefunctionalized biosensor to give a microfluidic device; coupling a gate electrode to the polymer single nanowire, wherein a solution in communication with the gate electrode and polymer single nanowire serves as a liquid electrolyte gate; and tuning a gate voltage applied to the gate electrode.

In another aspect of a preferred embodiment of the present disclosure, a biomarker detection device comprises: a microfluidic biosensor further comprising a biomarker functionalized polymer single nanowire connecting a pair of gold electrodes on a silicon wafer; the polymer single nanowire coupled to a gate electrode by a liquid electrolyte gate; a tunable gate voltage connected to the gate electrode; and software configured to receive input of the conductivity/resistivity of the polymer single nanowire and report a response for results of the conductivity/resistivity of the polymer single nanowire. Preferably, the reported response is outside a predetermined level. Additionally, the biomarker is preferably selected from the group consisting of B-type natriuretic peptide, myoglobin (Myo), cardiac troponin (cTpI), and creatine kinase (CK-MB). Further, such biomarker detection device may additionally comprise a wireless communication component.

BRIEF DESCRIPTION OF THE DRAWINGS

The present disclosure is illustrated by way of example and not limitation in the figures of the accompanying drawings, in which:

FIG. 1 is general illustration of a preferred method of fabrication of a polymer single nanowire on a silicon wafer on a 4 inch silicon wafer: (a) e-beam pattern on Si wafer, (b) chemical growth of nanofiber thin film (ref. 1), (c) nanofiber thin-film deposited on Si wafer, and (d) a lift-off process.

FIG. 1(b) represents the chemical growth of a nanofilm on the 4-inch wafer that will ultimately result in single nanowires of the embodiment of FIG. 1a.

FIG. 1(c) shows the nanofilm deposited on the wafer after the process in 1(b)

FIG. 2 (a) is a digital image of 4 inch silicon wafer with deposited gold electrodes of a preferred embodiment of the present disclosure. Digital and SEM images of (a) 4 inch Si wafer with deposited gold electrodes, (b) a single slice (1 cm×1 cm) with 16 pairs of gold electrode, (c) a single nanowire grown between electrodes—the distance between gold electrodes shows 5 micron, and (d) a single with 100 nm in width.

DETAILED DESCRIPTION OF PREFERRED EMBODIMENTS

The following description, taken in conjunction with the referenced drawings, is presented to enable one of ordinary skill in the art to make and use the disclosure and to incorporate it in the context of particular applications. Various modifications, as well as a variety of uses in different applications, will be readily apparent to those skilled in the art, and the general principles, defined herein, may be applied to a wide range of aspects. The present disclosure is not intended to be limited to the aspects disclosed herein. Instead, it is to be afforded the widest scope consistent with the disclosed aspects.

In a preferred embodiment of the present disclosure, a main component of the BNP wireless system is a polymer single nanowire sensor able to quantitatively and qualitatively measure BNP levels with high sensitivity and great specificity. Further, a preferred method of the present disclosure utilizes label-free sensing using conducting polymer field effect transistors (FETs) for cost-effective and simple assays, and a localizing surface modification method using shadow mask for increased flexibility of biosensor development.

Single Polymer Nanowire Fabrication

Figure 1A:
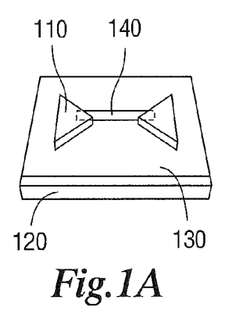
FIG. 1(a) shows an electron beam pattern on 4-inch silicon wafer, having a PMMA coating, as drawn between gold electrodes of a preferred embodiment of the present disclosure.

Referring now to FIG. 1, in a preferred embodiment of the present disclosure, gold electrodes 110 are patterned on a silicon wafer 120 by a photolithography lift-off process as is known in the art. The silicon wafer 120 is then prepared for electron-beam patterning by a spin coating of polymethylmethacrylate (PMMA) resist 130 onto the silicon wafer 120. Next, e-beam lithography is used to create nanochannels 140 between paired gold electrode pairs as is illustrated in FIG. 1(a).

In a separate container, aniline monomer is added into 15 mL of aqueous perchloric acid and stirred for 30 min while holding the solution at a steady cold temperature in the range of 0 to 5° C. so that a uniform mixture is created (the "polymerization solution").

In still another container, ammonium persulfate, a strong oxidant, is dissolved in an aqueous perchloric acid solution and cooled to a temperature in the range of 0-5° C. (the "oxidant solution").

Figures 1B, 1C:
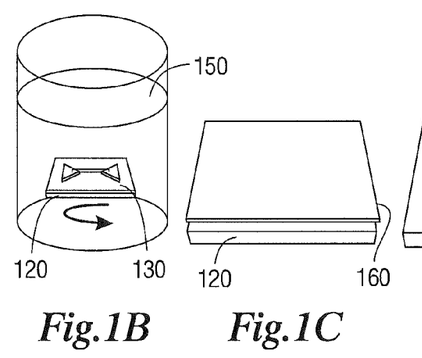

Referring now to FIG. 1(b), in a preferred method of the present disclosure, the silicon wafer 120, having a PMMA resist coating 130 with electron beam patterning on it, is placed into the polymerization solution and then the oxidant solution is rapidly added, with the resulting solution 150 then being stirred for 3-24 hours, but preferably 4 hours, at a temperature in the range of 0-5° C. Preferably, the ratio of aniline monomer to ammonium persulfate in this resulting solution is 3:1.

Figure 1D:
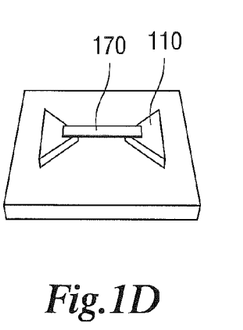
FIG. 1(d) shows a polymer single nanowire formed between the gold electrodes after the lift-off process is complete, showing that the nanofilm remains deposited inside the electron beam pattern.

As a result of such preferred method of the present disclosure, a thin layer of electrically conducting polyaniline (PANI) film 160 becomes coated on the wafer 120, as is illustrated in FIG. 1(c). The coated wafer is then removed from the solution 150 and washed with deionized water to remove extra PANT precipitate. Next, the wafer 120 is cut into one centimeter squares, each square having sixteen pairs of working electrodes plus four gate electrodes with a nanochannel having formed in between each pair. Next, the wafer is immersed in acetone for 5-10 minutes to remove the PMMA and resin, revealing single nanowires 170 between each electrode pair 110 according to the PMMA patterns. Finally, the non-patterned PANI film is removed from the wafer by ultrasonication, each having sixteen pairs of working electrodes with one nanowire across each pair, an example of which is shown in FIG. 1(d).

Figure 2A:
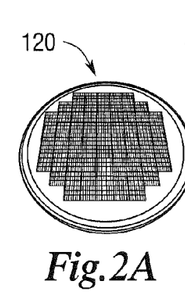
Figure 2B:
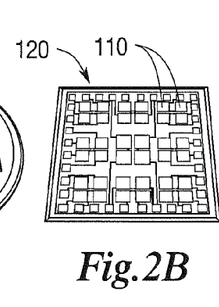
FIG. 2(b) is a digital image of a single slice (1 cm×1 cm) of a silicon wafer according to a preferred embodiment of the present disclosure with sixteen pairs of gold electrodes.
Figure 2C:
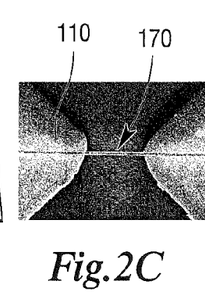
FIG. 2(c) is a scanning electron microscope (SEM) image of a polymer single nanowire according to a preferred embodiment of the present disclosure grown between electrodes, the distance between the electrodes is five microns.
Figure 2D:
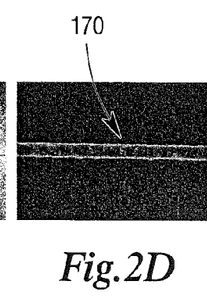
FIG. 2(d) is an SEM image of a polymer single nanowire of 100 nm in width according to a preferred embodiment of the present disclosure.

Referring now to FIG. 2 as a preferred embodiment, the gold electrodes 110 are patterned on a four-inch silicon wafer 120 (FIG. 2a). The silicon wafer 120 is then prepared for electron-beam patterning by a spin coating of polymethylmethacrylate (PMMA) resist 130 onto the wafer 120. For nanofiber thin-film deposition on the surface of the exposed $SiO_2$/PMMA [1], the oxidant, ammonium persulfate (APS), was dissolved in 5 mL of aqueous perchloric acid solution and cooled to 0° C. Aniline monomer was added into 15 mL of aqueous perchloric acid and stirred for 30 min while still holding the solution at a steady 0° C. to form a uniform mixture. Then wafers (chips) 120 were placed in the solution and the polymerization was performed by rapid addition of the precooled oxidant solution followed by stirring for 3-24 h at 0° C. After the polymerization, a thin layer of PANI film was coated on the chip. The whole wafer was then placed into acetone for 5-10 min. Afterward, PANI nanowires 170 were obtained using sonication to remove the non-patterned PANT film In a preferred embodiment of the present disclosure, the 4-inch wafer is cut into slices with 1 cm by 1 cm size as shown in FIG. 2(b). Each slice has sixteen pairs of working electrodes with one nanochannel across each pair. After lift-off in acetone, the single nanowires 170 are bridged between gold electrodes (FIG. 2(c)) according to the PMMA patterns. FIG. 2(d) shows a uniformly formed single nanowire 170 which can be mass produced with reproducibility.

As a result of this preferred process of the present disclosure, a plurality of polyaniline nanowires 170 are formed between the gold electrodes 110 on the wafers 120. Importantly, these nanowires 170 are highly uniform in size, for example, preferably they may all be roughly 100 nm in width and approximately 8 micrometers in length. These diameters and lengths can be controlled with the electron beam patterning process. Electron microscopy reveals that there is a plurality of nanofibers on each nanowire, which significantly increases the surface area of each nanowire and results in a high surface to volume ratio, which is advantageous for biosensor applications, for example. An additional advantage of polymer nanowires is they are hydrophilic which enables easy surface modification.

Functionalization of Nanowires for Use as Biosensors

Once the PANI nanowires have been created, they can be functionalized for specific biosensing applications by attaching appropriate antibodies, aptamers, or other chemicals to the surface of the nanowire such that when the targeted molecule comes into contact with the nanowire, it binds to it and changes its electrical conductance.

By way of example, and in a preferred embodiment, a sensor can be created to detect a negative myocardial event in people with a history of heart disease since BNP has such a well-known correlation with heart muscle distress. In order to be able to sense an increase in BNP in the blood, without running a test in a hospital or outpatient setting, a nanosensor can be created using nanowires that have been properly functionalized.

For surface modification of the nanowire to detect BNP, either BNP monoclonal antibodies (mAbs) or BNP aptamers preferably are covalently bonded onto the surface of the polymeric nanowires via surface immobilization. A mixture solution of the cross-linkers 1-ethyl-3-(3-dimethylaminopropyl) carbodiimide) (EDC) and N-hydroxysuccinimide (NHS) (0.2/0.2 M) and BNP mAbs (100 µg/mL) or BNP aptamer (100 µg/mL) preferably is placed on top of the PANI nanowires prepared as described herein and incubated at room temperature in a dark room for 3 hrs. The nanowires were then rinsed with a phosphate buffered saline (PBS) solution and deionized water to eliminate any parasitic non-immobilized BNP mAbs (or BNP aptamers). After the surface immobilization, the nanowires are soaked in a high concentration of bovine serum albumin (BSA) (2 mg/mL) for 30 min to block non-specific protein interactions with the nanowires.

Similarly, BNP monoclonal antibodies (mAbs) preferably were covalently bonded onto the surface of the PANI nanowires via surface immobilization. A mixture solution of EDC/NHS (0.2/0.2 M) with IgG mAbs (100 µg/mL) was placed on top of PANI nanowires and incubated at room temperature in a dark room for 3 hrs. The PANI nanowires were then rinsed by PBS solution and deionized water to eliminate any parasitic non-immobilized BNP mAbs. After the surface immobilization, the PANT nanowires were soaked in a high concentration of BSA (2 mg/mL) for 30 min to block non-specific protein interactions with the nanowires.

Protection of Functionalized Nanowires During Creation of Microfluidic Sensor

Once the functionalized PANI nanowires have been created, they must be placed into an electrical circuit to enable their sensing capabilities to be utilized. Because the sensor will be used in the presence of blood to detect a biomarker (such as BNP in the presently preferred embodiment), a microfluidic sensor serves this purpose best. Integrating polydimethylsiloxane (PDMS) and a nanowire sensor containing pre-functionalized biosensors into a microfluidic device with irreversible sealing is challenging, however, because the sealing process requires an oxygen plasma treatment, which, until now, usually destroyed the pre-functionalized biosensors. A preferred process of the present disclosure, however, has overcome this difficulty.

Figure 3A:
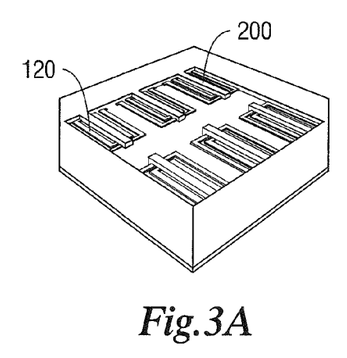
FIG. 3(a) is a schematic illustration of the plasma treatment of a shadow mask protected chip of a preferred embodiment of the present disclosure.
Figure 3B:
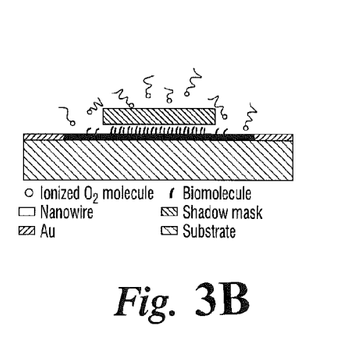
FIG. 3(b) is a schematic illustration of the plasma treatment of a shadow mask protected chip in an enlarged view, where the bio-functionalized nanowire is protected by the shadow mask according to a preferred embodiment of the present disclosure.

Referring now to FIG. 3, the functionalized PANI nanowires are covered with a bio-shielding (shadow) mask 200 during the incorporation of poly(dimethylsiloxane) PDMS microfluidics in order to protect the active sensor component at the antibody-modified locations. In a preferred embodiment, the mask 200 is the same size as the Si wafer slice 120 (one inch square) and is constructed of an aluminum substrate via a micro-manufacturing process as is known in the art, and preferably is manually placed on top of the wafer 120.

Figure 4:
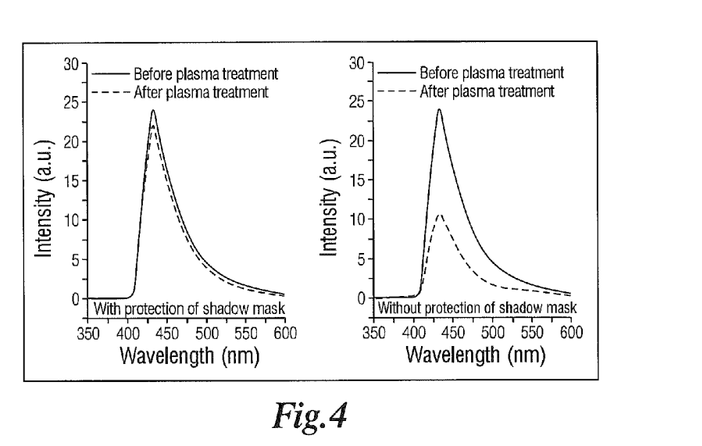
FIG. 4 are graphs illustrating the fluorescence intensity of samples before and after plasma treatment with (left graph) and without (right graph) the protection of a shadow mask for according to a preferred embodiment of the present disclosure.

Ordinarily, the sealing process involves $O_2$ plasma treatment which usually destroys the pre-functionalized biosensor. The protection effects of using the shadow mask were evaluated by comparing the resistance and fluorescence intensity (FIG. 4) of samples treated by $O_2$ plasma both with and without the shadow mask. In the absence of a shadow mask, the nanowires were destroyed, resulting in an infinite resistance and reduced fluorescence intensity. In contrast, the shadow mask protected the nanowires and thus exhibited small changes in the resistance and fluorescence intensity. The protected samples showed a recognizable sensitivity to the targets. This preferred method provides an easy way to prevent the deactivation of pre-functionalized biosensors for developing microfluidic devices with irreversible sealing and thus can be applied for various integrated microfluidic devices as will be readily apparent to those skilled in the art.

Increasing the Sensitivity of the Biosensors

In a preferred embodiment of the process of the present disclosure, the next step in creating a microfluidic biosensor, such as for BNP, is to create a field-effect-transistor (FET) structure employing the functionalized polymer single nanowire biosensor.

Figure 6:
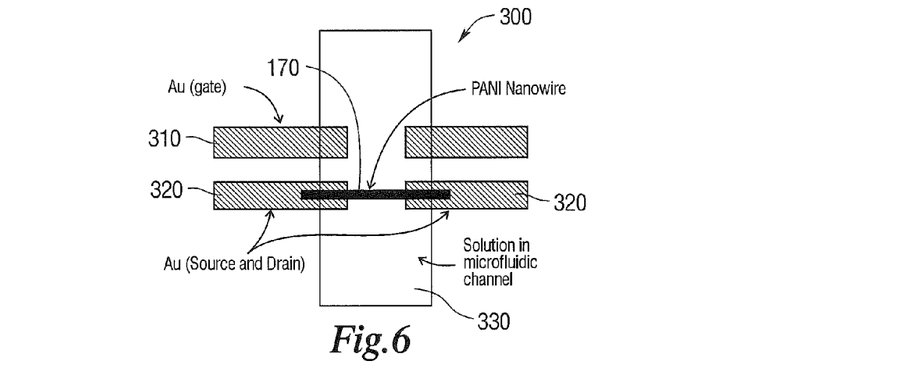
FIG. 6 is a schematic illustration of a field effect transistor structure employing a polymer single nanowire biosensor according to a preferred embodiment of the present disclosure, having two pairs of gold electrodes and one of them used as a gate electrode, with a biomolecule solution inside a microfluidic channel over the polymer single nanowire biosensor component. Schematically illustrated single nanowire FET structure; indicates two pairs of gold electrodes (310 and 320) and one of them was used for gate electrode (310), biomolecules solution (330) inside of microfluidic channel over single nanowire sensor component (170).

Referring now to FIG. 6, the single nanowire Ion-Selective FET structure (ISFET), or, simply, transistor, 300 of the present disclosure is established by using an extra gold electrode as a gate 310 structure. A gate voltage ($V_G$) is provided by a power supply and the gate 310 is separated from the source and drain electrodes 320 to modulate the current flow through the nanowire 170. The source-drain voltage ($V_{SD}$) generates the source-drain current, which is enhanced or quenched upon application of a given gate voltage.

For detection of a biomarker of interest, such as BNP, the microfluidic channel 330 is flooded with a phosphate buffer saline (PBS) solution containing the biomarker. When the biomarkers are then adsorbed into the sensing area of the nanowire 170, they chemically bind with the nanowire, locally changing the electrical charge of the nanowire, and thus its conductance, resulting in a change in the resistance between the source and drain 320.

The change in resistance (or conversely, conductance) of the nanowire depends on two important factors: (a) the semiconductor type of the nanowire, and (b) the net charge carried by the biomarker in the solution (i.e. the amount of biomarker in the blood). For example, the PANI nanowire in a presently preferred embodiment is a typical p-type material, and the BNP molecules are positively charged in the PBS (pH=7.4) due to its relatively high isoelectric point (pI=~9.8), therefore, the attachment of the BNP biomarkers onto the nanowire could decrease the hole carrier density in the nanowire, resulting in a resistance increase of the nanowire. Since there's a voltage across the source and drain, this change in resistance can be measured, signaling the concentration of biomarker in the solution. It should be noted that the resistance change occurs only in the section of the nanowire immediately under biomarker attachment. For this reason, a nanowire device is preferred over an easier-conceived larger cross-section device as it will be more sensitive to localized resistance changes.

Referring still to FIG. 6, the particular layout of the transistor 300, which, technically, is an ion-selective field-effect transistor is important for two key reasons: (i) the strong coupling of the gate 310 to the nanowire 170 and not the source and drain electrodes 320, as would be for a back-gate layout, allows very precise control of the nanowire 170 depletion. Thus, the transistor structure can be biased such that a change in resistance caused by the attachment of the cardiac marker induces a rapid and distinct change in the drain current at a constant drain voltage. As such, any charge generated by the presence of cardiac biomarkers will induce a charge in the channel of the FET structure. That charge, in turn, could enhance the inversion of the channel and permit greater current conduction, which offers a quantitative analysis mode and more sensitive operation than conventional two-electrode (diode) devices. Secondly, the biomolecular solution itself serves as the liquid electrolyte gate for the ISFET, hence simplifying fabrication and permitting greater standardization of the device performance via gate voltage ($V_G$) tuning.

A preferred single nanowire-based ISFET of the present disclosure will also permit great sensitivity because the coupling between the gate and binding events are related. Further, the ISFET, as shown in FIG. 3, will have better noise reduction performance because the electrodes in an ISFET are usually small with very small leakage currents. In addition, the ISFET performs an impedance transformation on the sensor chip, and transforms an input voltage to an output current (low impedance). Therefore, the signal leaving the ISFET is much less susceptible to noise.

As will be readily apparent to those skilled in the art, a nanowire FET biosensor (ISFET) constructed in accordance with the methods and materials disclosed is herein can also be functionalized to detect other important biomarkers such as Myo, cTnI and CK-MB which are other known biomarkers for cardiovascular diseases.

Sensor Performance Using Nanowire FET Microfluidic Devices

As discussed above, the prompt and accurate detection of the cardiac biomarker BNP plays a vital role in the diagnosis of myocardial infarction. To ensure target biomarker specificity, especially in the presence of similar markers, a single nanowire FET biosensor constructed in accordance with the methods and materials set forth in this disclosure was exposed to a number of different biomarkers, and then followed by BNP. As can be seen below, the biosensor was still able to detect the BNP.

Figure 5A:
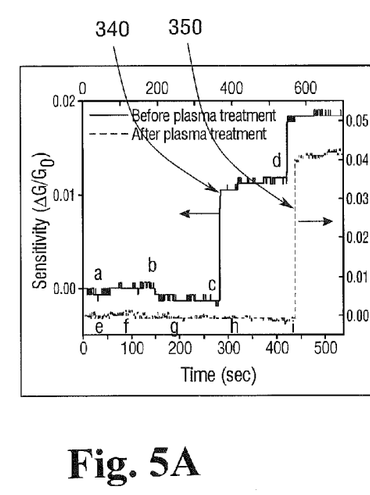
FIG. 5a illustrates the response of a polymer single nanowire biosensor according to a preferred embodiment of the present disclosure challenged with various proteins showing that such polymer single nanowire biosensor is selective for the functionalized biomarker. For detection of BNP (340 on left scale a: PBS, b: BSA of 100 ng/mL, c: BNP of 1 ng/mL, and d: BNP of 10 ng/mL; and 350 on right scale e: PBS, f: Myo of 1 ng/mL, g: cTnI of 1 ng/mL, h: CK-MB of 1 ng/mL, and i: BNP of 1 ng/mL), the nanowire biosensor responds to only BNP.
Figure 5B:
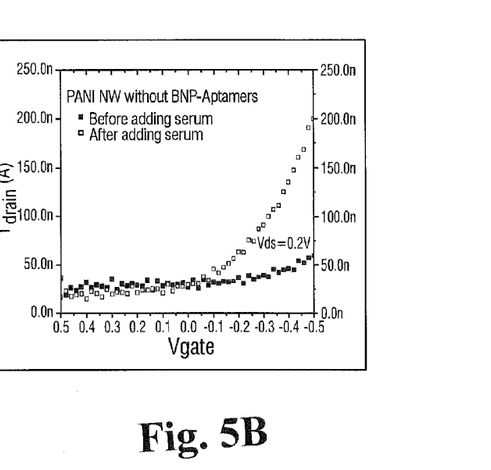
FIG. 5b illustrates a polymer field effect transistor (FET) characterization of a preferred polymer single nanowire biosensor of the present disclosure using human serum from high level of BNP patient. The solid squares are before adding serum, the hollow squares are after adding serum.

With reference to the results graph of FIG. 5, the sensor was challenged with the following proteins: a: PBS, b: BSA of 100 ng/mL, c: BNP of 1 ng/mL, d: BNP of 10 ng/mL, e: PBS, f: Myo of 1 ng/mL, g: cTnI of 1 ng/mL, h: CK-MB of 1 ng/mL, and i: BNP of 1 ng/mL. As can be seen by viewing the solid line 340 in cases a-d, a preferred single nanowire biosensor of the present disclosure responded significantly to BNP only. Likewise, the dotted line 350 demonstrates that a preferred single nanowire biosensor of the present disclosure provided significant responses, even in the presence of other (non-BNP) cardiac biomarkers including BSA. In order to apply for practical diagnosis, it is necessary to verify sensing performance in the presence of BSA (solid line 340 in FIG. 5 (*a*)), which is the most abundant protein in the serum and similar to human serum albumin, or non-target cardiac biomarkers.

Results from tests of preferred FETs using single nanowire biosensors of the present disclosure with respect to the sensing of those specific target proteins with non-target proteins for BNP are demonstrated in FIG. 5. The single nanowire biosensor was exposed to concentrations of BSA in the range of 1-100 ng/mL followed by each target proteins showing significant conductance change as shown in FIG. 5 (*a*) (solid line 340). In addition, preferred nanowire biosensors of the present disclosure show unique responses depending on specific mAbs on the single PANI nanowire in adding other cardiac biomarkers (dotted line 350. In the presence of non-target proteins, the nanowire biosensors have around $1\times10^3$-$1\times10^6$ fold specificity, which is lower than the value in the absence of non-target proteins but very acceptable for biosensing application. Non-specific binding of non-target proteins preferably is restrained by a blocking process whereby BSA (2 mg/mL) is coated on the surface of nanowire after post-functionalization. When properly configured, preferred single site-specific PANI nanowire biosensors disclosed herein displayed the marked ability to detect BNP and other biomarkers such as Myo, cTnI, and CK-MB within the presence of non-target proteins.

Human serum with high BNP levels was also characterized using the disclosed single nanowire FET structure. A single chip, measuring 1 cm by 1 cm with wire-bonded on socket, and containing several nanowires, was placed on a probe station and connected to a semiconductor device analyzer (Agilent Technologies B1500A) through three probes. A probe was attached to each of the source, drain, and gate electrodes. The source-drain voltage and gate voltage were provided and controlled by the semiconductor device analyzer, which also collected the source-drain current during the measurements. Typically, the gate voltage was swept from 0.5 V to −0.5 V with a 2 mV sweeping step and the source-drain voltage was scanned from 0 V to 0.5 V with a step of 0.1 V. A baseline of the FET sensor was first acquired by adding a PBS solution onto the sensor, and then the detection signal was obtained right after the addition of human serum sample containing BNP biomarkers. From the result, before adding to human serum with source-drain bias of 0.2V, the drain current was about 50 nA with a gate bias of −0.4V while the drain current increased by a factor of 4 when human serum sample with known high-concentration of BNP was exposed to the nanowire.

Upon examination of the $I_{sd}$-$V_G$ characteristics of this FET device before and after serum exposure, stronger electron-carrier gate response and a left-shift of the threshold voltage was observed. Both of these observations indicate that the addition of human serum led to strong electron accumulation on the PANI nanowire surface. These results confirm that the FET structure is preferable for incorporation into a scale-able and quantitative analyzing system for various biomarkers including various cardiac and cancer biomarkers.

Also, preferably, the single nanowire sensor fabrication method of the present disclosure is scalable to the substrate dimensions, and can be mass produced with reproducibility and without a post-assembly process requirement—a unique advantage over competing designs.

Preferred single nanowire biosensors of the present disclosure can also be used for other biomarker sensing applications because the ability to detect extremely low amounts of target biomolecules with high sensitivity down to a single molecule/particle with good specificity and at low cost. The keystone requirements to spur growth in the emerging field of biomedical devices. The single nanowire biosensors of the present disclosure provide an extremely sensitive transduction mechanism/transducer with enhanced specificity.

Wafer Scale Nanowire Fabrication

Figure 7:
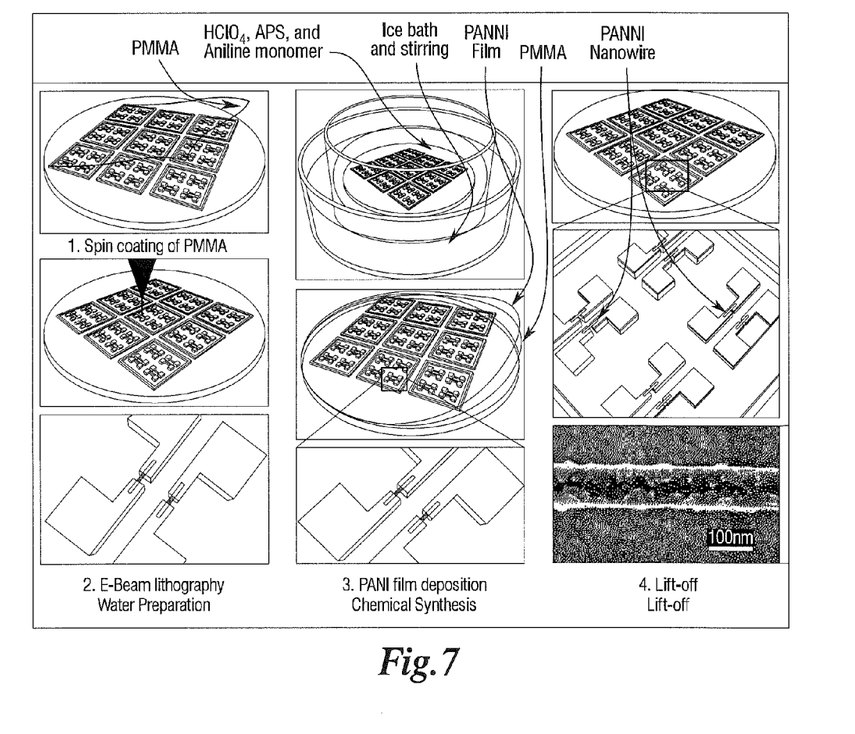
FIG. 7 is schematic illustration of the process flow for the fabrication of PANI NWs on a 4 inch wafer according to a preferred embodiment of the present disclosure.

As shown in FIG. 7, gold electrodes are patterned on a silicon wafer by a photolithography lift-off process as is known in the art. The silicon wafer is then prepared for electron-beam patterning by a spin coating of LOR and poly-methyl methacrylate (PMMA) resist onto the silicon wafer to form bi-layer photoresist. Next, e-beam lithography is used to create nanochannels between paired gold electrode pairs.

In a separate container, aniline monomer is added into 200 mL of aqueous perchloric acid and stirred for 30 min while holding the solution at a steady cold temperature in the range of 0 to 5° C. so that a uniform mixture is created (the "polymerization solution").

In another container, ammonium persulfate, a strong oxidant, is dissolved in an aqueous perchloric acid solution and cooled to a temperature in the range of 0-5° C. (the "oxidant solution").

The silicon wafer, having a bilayer photoresist coating with electron beam patterning on it, is placed into the polymerization solution and then the oxidant solution is rapidly added, with the resulting solution then being stirred for 3-24 hours, but preferably 4 hours, at a temperature in the range of 0-5° C. Preferably, the ratio of aniline monomer to ammonium persulfate in this resulting solution is 3:1.

As a result of this process, a thin layer of electrically conducting polyaniline (PANI) film becomes coated on the wafer. The coated wafer is then removed from the solution and washed with deionized water to remove extra PANI precipitate. Next, the wafer is immersed in acetone for 5-10 minutes to remove the PMMA and resin, revealing single nanowires between each electrode pair according to the PMMA patterns. Finally, the non-patterned PANI film is removed from the wafer by ultrasonication, leaving patterned PANT NWs across the electrode pairs.

BNP Sensing

Experiment: NT-proBNP detection in buffer solution.

The detection of the NT-proBNP biomarker in phosphate buffer saline (PBS, pH=7.20) was investigated using PANI-NW FET sensors. A chip containing PANI-NWs was placed on a probe station and connected to a semiconductor device analyzer (Agilent Technologies B1500A) via three probes. One of each probe was attached to the source, drain, and gate electrodes. The source-drain voltage and gate voltage were provided and controlled by the semiconductor device analyzer, which also collected the source-drain current during the analysis. For typical FET measurements, the Au electrodes connected to the NW were utilized as source and drain electrodes, while another Au electrode was used as the gate electrode. A PBS solution was added onto the sensor at first. Simultaneously, the drain current (Id) of the NW was monitored by a sweep with gate voltage (Vg) from 0.5 V to –0.5 V and a drain bias (Vd) of 0.5 V. To complete the experiment, another Id-Vg measurement was performed after the addition of NT-proBNP solution onto the sensor. All the measurements were carried out at ambient conditions.

Figure 8:
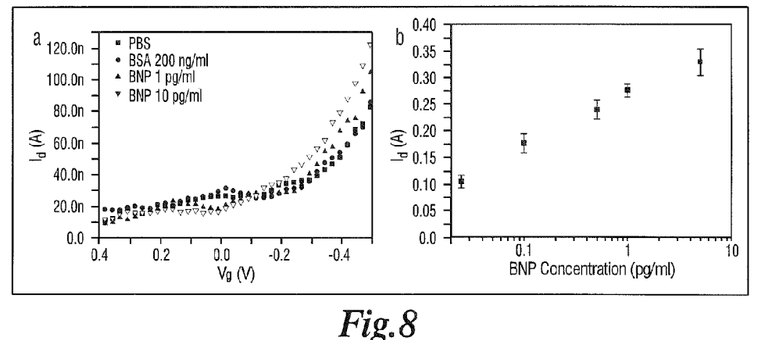
FIG. 8a shows the plot of the drain-source current versus gate voltage of the PANI-NWAs FET in PBS buffer solution according to a preferred embodiment of the present disclosure.
FIG. 8b shows the plot of normalized changes of drain current as a function of the NT-proBNP concentration ($\Delta Id/Id0$, where $Id0$ is the stabilized drain current of the NW in PBS solution) according to a preferred embodiment of the present disclosure.

Results FIG. 8a shows the plot of the drain-source current versus gate voltage of the PANI-NWAs FET in PBS buffer solution. The drain current Id rises upon increasing negative Vg at positive drain-source voltage (Vd), indicating a p-type behavior of the PANI-NWAs FET devices. Upon the addition of highly concentrated nonspecific target molecule BSA, no Id changes were observed. In contrast, the sensor showed significant increase in Id upon the addition of NT-proBNP solutions, indicating the high specificity of this sensor. When the NT-proBNP concentration was progressively increased, consistent increases in Id were also observed. FIG. 8b shows the plot of normalized changes of drain current as a function of the NT-proBNP concentration (ΔId/Id0, where Id0 is the stabilized drain current of the NW in PBS solution). As shown, the PANI-NWs exhibited a wide dynamic sensing range from 25 g/mL to 5 pg/mL The lowest detectable BNP concentration of 25 g/mL is much lower than that obtained by the surface plasma resonance sensor (5 pg/mL). This ultra-high sensitivity and low detection limit presented by the FET sensors should be ascribed to the unique dimension of the PANI-NWs.

Experiment: NT-proBNP detection in whole blood samples.

In this experiment, the NT-proBNP purchased from Sigma-Aldrich was spiked in normal human blood. The same setup and method used in the NT-proBNP detection in PBS solution was employed for this test with the exception of the applied drain and gate voltages.

Figure 9:
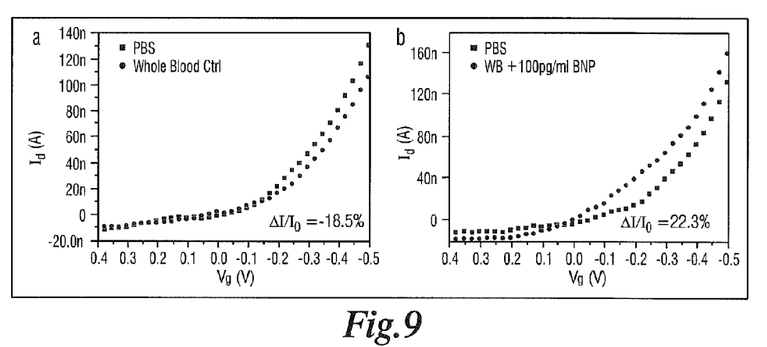
FIG. 9a comprises a $I_d$-$V_g$ curve of PANI NW FET sensors responding to health whole blood control sample according to a preferred embodiment of the present disclosure.
FIG. 9b comprises a $I_d$-$V_g$ curve of PANI NW FET sensors responding to whole blood sample containing 100 pg/ml NT-proBNP according to a preferred embodiment of the present disclosure.
Figure 10:
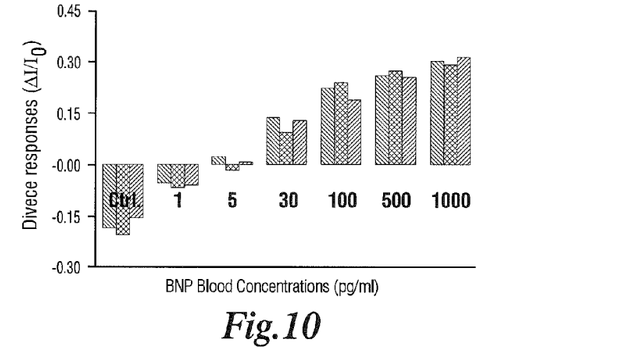
FIG. 10 comprises a graph showing normalized drain current change of the NW FET sensors according to a preferred embodiment of the present disclosure as a function of BNP blood concentration with respect to the baseline in PBS solution.

Results The Id-Vg curves of the PANI-NW FET sensors responding to whole blood samples are shown in FIGS. 9a and 9b. It is clearly shown in the figures that the Id of the NW decreased (~18.5%) after the addition of the whole blood control sample referring to that obtained in PBS solution, which is due to the high viscosity and ionic concentrations in whole blood. When a NT-proBNP (100 pg/ml) whole blood sample was added onto the sensor, an increase in Id (~22.3%) was observed. The negative effect on the NW caused by the whole blood was counteracted by the addition of NT-proBNP because the binding of negatively charged NT-proBNP resulted in positive current changes in the NW. The normalized drain current change of the NW FET sensors as a function of NT-proBNP blood concentration with respect to the baseline in PBS solution is given in FIG. 10. As shown in the graph of FIG. 10, positive response of the NW was shown when the NT-proBNP concentration was higher than 5 pg/ml. More positive current changes can be observed as the NT-proBNP concentration increased from 5 pg/ml to 1 ng/ml. These results indicate the feasibility of using the PANI NW FET biosensor to detect BNP biomarker in whole blood.

Experiment 3. BNP detection in patient's serum samples

The sensor's performance was also investigated using patients' serum samples collected before and after clinical treatment. The same setup and method used in the NT-proBNP detection in PBS solution was employed for the test with the exception of the applied drain and gate voltages.

Figure 11:
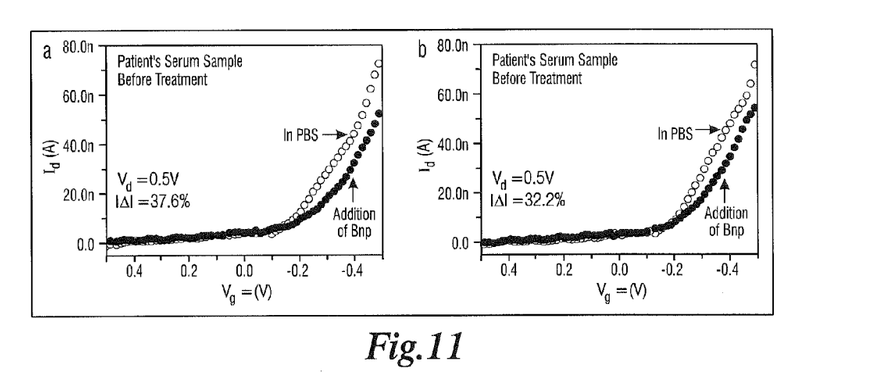
FIG. 11a comprises a $I_d$-$V_g$ curve of NW-FET sensors according to a preferred embodiment of the present disclosure corresponding to PBS solution and two serum samples before medical treatment.
FIG. 11b comprises a $I_d$-$V_g$ curve of NW-FET sensors according to a preferred embodiment of the present disclosure corresponding to PBS solution and two serum samples after medical treatment.

Results The Id-Vg curves of the NW FET sensor's response to the serum samples before and after medical treatment are shown in FIG. 11a. The drain currents before medical treatment in PBS and patient serum were 78.7 nA and 49.1 nA, respectively, at Vg=–0.5 V and Vd=0.4 V, showing a ~37.6% change. BNP molecules in the blood were positively charged in serum because it has relatively higher pH (~11.46) than the solution pH (~7.4). The binding of BNP molecules to the NW introduced positive charges on the p-type NW, which caused the hole depletion in the NW, resulting in a decrease in Id of the NW. A smaller decrease (~32.2%) was observed (FIG. 11b) in the patient serum after medical treatment with respect to the baseline in PBS solution, indicating a lower level of BNP concentration in the patient serum after treatment.

Figure 12A:
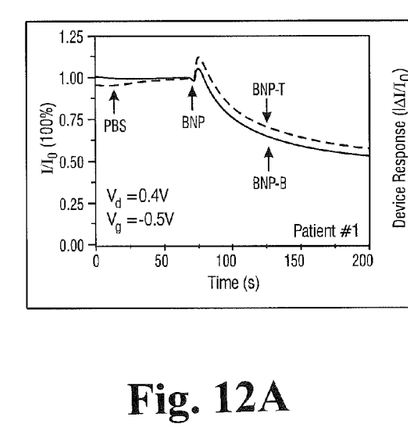
FIG. 12a comprises a graph showing real-time response of the PANI NW FET sensor according to a preferred embodiment of the present disclosure responding to patient's serum sample collected before and after medical treatment.
Figure 12B:
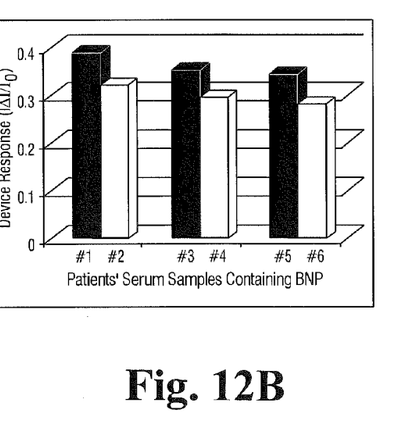
FIG. 12b comprises a graph showing a comparison of the responses of devices according to a preferred embodiment of the present disclosure to serum samples of three different patients. It is clearly shown in the graph that the patients' BNP levels were decreased after medical treatment.

To verify the observations from Id-Vg measurements, real-time detection of the BNP in the patients' serum samples was also performed using PANI-NW FET sensors. The drain currents of the NWs were monitored versus time at drain voltage of 0.4 V and gate bias of –0.5 V. The normalized responses of the NWs for two patients before and after medical treatments are shown in FIG. 12a. As shown in the figures, the Id of the NW was stable in PBS. After addition of a serum sample, a notable decrease in the Id is observed. The Id decreased ~40% within one minute after the addition of the serum samples. The figures also show clear comparisons of the drain current changes of the sensors responding to the patients' serum samples at different conditions, where less Id decrease is visible for the serum sample of patient after medical treatment (blue line) than that of before treatment. These results confirm the findings in previous experiments. Similar changes were observed from other patient serum samples before (#1, #3, #5) and after (#2, #4, #6) treatment as shown in FIG. 12b. These results indicate that the NW-FET sensors are capable of determining different BNP levels in patient serum samples.

Kits for Home Use

The ISFET of the present disclosure preferably can be incorporated into a home use device or kit, in much the same way that modern day glucose hand-held monitors are used, wherein a small amount of blood can be analyzed at any time, or on a regular basis, in the home. Preferably, such home kit will be connected (wirelessly or otherwise) to an analysis software application (resident on the user's home computer or accessed via a SAAS model) such that an elevated BNP level in the patient's blood will trigger a message (whether delivered to the patient, their designee or their primary health care provider) indicating the need for further investigation in response to a possibly imminent negative cardiac event. An additional benefit of a regular monitoring paradigm for patients with elevated risk is that the physician will then have the capability to consider the history of the patient's BNP levels in fashioning an emergent response or other treatment plan.

Biomarker (BNP) Measurement Device/System

Figure 13:
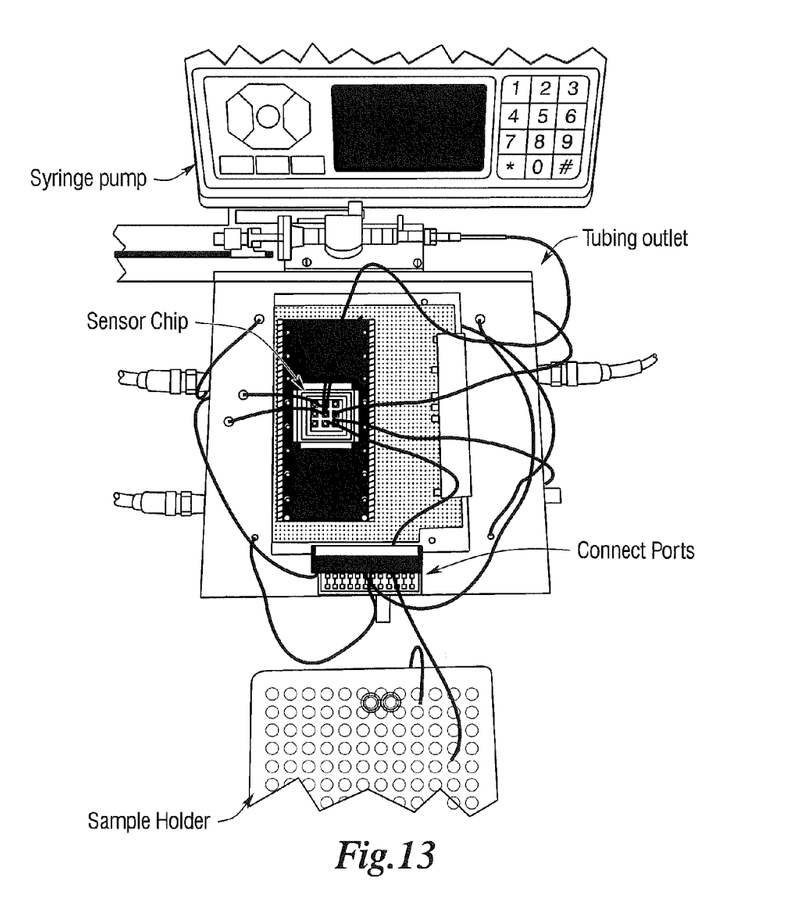
FIG. 13 shows a preferred measurement device/system having a PANI NW FET sensor according to a preferred embodiment of the present disclosure.

As shown in FIG. 13, a measurement device/system according to a preferred embodiment of the present disclosure has a sensor chip wire-bonded to a chip holder, which connects to the data acquisition unit. The sensor chip can be easily integrated into this system. Microfluidic channels were attached to the sensor chip, and tubing was used to connect the microfluidic channel and the syringe pump. The syringe pump can withdraw the solution from the inlet with desired flow rate. Such measurement device/system simplifies the measuring operations and improves the measurement reliability for the biomarker by reducing external interference.

It should be understood that while this disclosure has been described herein in terms of specific, preferred embodiments set forth in detail, such embodiments are presented by way of illustration of the general principles of the disclosure, and the disclosure is not necessarily limited thereto. Certain modifications and variations in any given material, process step or chemical formula will be readily apparent to those skilled in the art without departing from the true spirit and scope of the present disclosure, and all such modifications and variations should be considered within the scope of the claims that follow.

We claim:

1. A method of fabricating a plurality of polymer single nanowires having elevated surface to volume ratios, comprising the steps of:
   spin coating a polymethylmethacrylate resist onto a silicon wafer patterned with a plurality of gold electrode pairs;
   creating a nanochannel using e-beam lithography between each pair of the plurality of gold electrode pairs;
   placing the silicon wafer into a first solution maintained at a temperature between 0° C. and 5° C. and comprising an aniline monomer in an aqueous perchloric acid;
   reacting the first solution with a second solution maintained at a temperature between 0° C. and 5° C. and comprising ammonium persulfate in an aqueous perchloric acid to give a polyaniline film coated wafer; and
   cleaning the polyaniline film coated wafer of polymethylmethacrylate resist and polyaniline film to give a plurality of gold electrode pairs with a connecting polymer single nanowire having an elevated surface to volume ratio between each of the plurality of gold electrode pairs.

2. The method of claim 1, wherein each of the polymer single nanowires has a uniform diameter.

3. The method of claim 1, wherein each polymer single nanowire has a diameter of about 100 nanometers and a length of about 8 micrometers.

* * * * *